US011248262B2

(12) United States Patent
Fang et al.

(10) Patent No.: US 11,248,262 B2
(45) Date of Patent: Feb. 15, 2022

(54) METHOD FOR GENERATING A RNA-SEQUENCING LIBRARY

(71) Applicant: Qiagen GmbH, Hilden (DE)

(72) Inventors: Nan Fang, Hilden (DE); Bernhard Noll, Hilden (DE); Katja Heitz, Hilden (DE)

(73) Assignee: QIAGEN GmbH, Hilden (DE)

( * ) Notice: Subject to any disclaimer, the term of this patent is extended or adjusted under 35 U.S.C. 154(b) by 469 days.

(21) Appl. No.: 15/750,345

(22) PCT Filed: Aug. 24, 2016

(86) PCT No.: PCT/EP2016/069997

§ 371 (c)(1),
(2) Date: Feb. 5, 2018

(87) PCT Pub. No.: WO2017/032808

PCT Pub. Date: Mar. 2, 2017

(65) Prior Publication Data

US 2018/0230527 A1 Aug. 16, 2018

(30) Foreign Application Priority Data

Aug. 24, 2015 (EP) .................................... 15182234

(51) Int. Cl.
*C12Q 1/68* (2018.01)
*C12Q 1/6869* (2018.01)
*C12Q 1/6855* (2018.01)

(52) U.S. Cl.
CPC ......... *C12Q 1/6869* (2013.01); *C12Q 1/6855* (2013.01)

(58) Field of Classification Search
CPC ........ C12Q 2525/186; C12Q 2525/191; C12Q 1/6869; C12Q 1/6855; C12Q 2521/107
See application file for complete search history.

(56) References Cited

U.S. PATENT DOCUMENTS

2002/0090618 A1* 7/2002 Smith .................. C12N 9/1276 435/6.11
2004/0121364 A1* 6/2004 Chee .................... C12Q 1/6827 435/6.12
2004/0265870 A1* 12/2004 Lee ........................ C07H 21/02 435/6.1
2005/0170373 A1* 8/2005 Monforte ............. C12Q 1/6809 435/6.14
2005/0272074 A1* 12/2005 Arezi ................... C12N 9/1276 435/6.11
2007/0031865 A1* 2/2007 Willoughby ....... C12N 15/1096 435/6.1
2009/0053775 A1* 2/2009 Dahl .................... C12Q 1/6865 435/91.51
2009/0093378 A1* 4/2009 Bignell ................ C12Q 1/6869 506/23
2011/0081704 A1* 4/2011 Smith .................. C12N 9/1276 435/194
2012/0010091 A1 1/2012 Linnarson
2014/0106433 A1* 4/2014 Walder ................. C12Q 1/6853 435/188
2014/0113332 A1* 4/2014 Betts ....................... C12P 19/34 435/91.5
2014/0287468 A1* 9/2014 Richard ............... C12Q 1/6806 435/91.53
2015/0011396 A1* 1/2015 Schroeder ............ C12Q 1/6855 506/2
2015/0087027 A1* 3/2015 Makarov .............. C12Q 1/6806 435/91.3
2015/0111789 A1* 4/2015 Betts .................. C12N 15/1096 506/26
2015/0275267 A1* 10/2015 O'Neil ................. C12Q 1/6806 506/2

FOREIGN PATENT DOCUMENTS

WO WO-2004033669 A2 * 4/2004 ........... C12Q 1/6841
WO WO-2007091064 A1 * 8/2007 ........... C12Q 1/6806

OTHER PUBLICATIONS

Islam S, Kjallquist U, Moliner A, Zajac P, Fan JB, Lonnerberg P, Linnarsson S. Highly multiplexed and strand-specific single-cell RNA 5' end sequencing. Nature protocols. May 2012; 7 (5):813-28. (Year: 2012).*
NEBNext DNA Library Prep Master Mix set for 454 Instruction manual pp. 1-20 (2012, New Englend Biolabs) (Year: 2012).*
Superscript II RNase H—Reverse Transcriptase Cat. No. 18064-014 by Life Technologies (2012) (Year: 2012).*

(Continued)

*Primary Examiner* — Teresa E Strzelecka
*Assistant Examiner* — Olayinka A Oyeyemi
(74) *Attorney, Agent, or Firm* — Rankin, Hill & Clark LLP

(57) ABSTRACT

The invention refers to a novel method of preparing strand-specific RNA-sequencing libraries that can be used to identify DNA coding and non-coding strands that are transcribed to RNA. Such strand-specific RNA-sequencing libraries are especially useful in discovering anti-sense RNA and non-coding RNA. Random primer oligonucleotides, covalently coupled to a moiety, which blocks ligation, are used for RT reaction or the subsequent generation of the second DNA strand so that only one strand of the generated double-stranded DNA is ligated to sequencing adapters at the 5' nucleotide and sequenced by paired-end sequencing.

5 Claims, 9 Drawing Sheets

(56) References Cited

OTHER PUBLICATIONS

Harismendy O, Frazer KA. Method for improving sequence coverage uniformity of targeted genomic intervals amplified by LR-PCR using Illumina GA sequencing-by-synthesis technology. Biotechniques. Mar. 2009; 46(3):229-31. (Year: 2009).*

Dean et al., 2001. Rapid amplification of plasmid and phage DNA using phi29 DNA polymerase and multiply-primed rolling circle amplification. Genome research, 11(6), pp. 1095-1099. (Year: 2001).*

Islam, Saiful et al., "Highly multiplexed and strand-specific single-cell RNA 5'end sequencing," Nature Protocols, May 2012, p. 813-828, vol. 7 issue 5, Nature Publishing Group, Great Britain.

Picelli, Simone et al., "Full-length RNA-Seq from single cells using Smart-seq2," Nature Protocols, Jan. 2014, p. 171-181, vol. 9 issue 1, Nature Publishing Group, Great Britain.

Han, Jing et al., "Novel multiple 5'-amino-modified primer for DNA microarrays," Genomics, Aug. 2005, p. 252-258, vol. 86 issue 2, Academic Press, USA.

Von Nickisch-Rosenegk, Marcus et al., "Reverse transcription-polymerase chain reaction on a microarray: The integrating concept of active arrays," Analytical and Bioanalytical Chemistry, May 2008, p. 1671-1678, vol. 391 issue 5, Springer, Germany.

Harismendy, Olivier et al. "Method for improving sequence coverage uniformity of targeted genomic intervals amplified by LR-PCR using Illumina GA sequencing-by-synthesis technology," Biotechniques, Mar. 2009, p. 229-231,vol. 46 No. 3, Scripps, USA.

Levin, Joshua Z. et al. "Comprehensive comparative analysis of strand-specific RNA sequencing methods," Nature Methods, Sep. 2010, p. 709-715, vol. 7 No. 9, SpringerNature, Germany.

Sultan, Marc et al. "A simple strand-specific RNA-Seq library preparation protocol combining the Illumina TruSeq RNA and the dUTP methods," Biochemical and Biophysical Research Communications, Jun. 2012, p. 643-646, vol. 422 issue 4, Elsevier, The Netherlands.

Notice of Reasons for Rejection dated Mar. 18, 2020 for the corresponding Japanese Patent Application No. 2018-502077; translation only.

Islam, S. et al., "Characterization of the single-cell transcriptional landscape by highly multiplex RNA-seq", Genome Research, May 4, 2011, pp. 1160-1167, vol. 2, Cold Spring Harbor Laboratory Press, New York, US; Cited in Japanese Office Action.

* cited by examiner

| | |
|---|---|
|  | 5´ Spacer 18 |
|  | 3´ Spacer 18 |
|  | 5´ Spacer 9 |
|  | 3´ Spacer 9 |
|  | 5´ C6-Spacer |
|  | 3´ C6-Spacer |
|  | 5´ C3-Spacer |
| | 3´ C3-Spacer |

FIG. 5 (continues on additional pages)

| Structure | Name |
|---|---|
| HO–(CH2CH2O)6–P(=O)(O⁻)~ | 5´ Spacer 18 |
| ~P(=O)(O⁻)–O–(CH2CH2O)5–CH2CH2OH | 3´ Spacer 18 |
| HO–(CH2CH2O)3–P(=O)(O⁻)~ | 5´ Spacer 9 |
| ~P(=O)(O⁻)–O–(CH2CH2O)2–CH2CH2OH | 3´ Spacer 9 |
| HO–(CH2)6–O–P(=O)(O⁻)~ | 5´ C6-Spacer |
| ~P(=O)(O⁻)–O–(CH2)6–OH | 3´ C6-Spacer |
| HO–(CH2)3–O–P(=O)(O⁻)~ | 5´ C3-Spacer |
| ~P(=O)(O⁻)–O–(CH2)3–OH | 3´ C3-Spacer |

| | |
|---|---|
|  | 5´ d spacer |
|  | 3´ d spacer |
|  | 5´ r spacer |
|  | 3´ r spacer |
| | DADE-linker |

FIG. 5 (continued)

| | |
|---|---|
| | 5′-5′ inverted nucleotide |
| | 5′ C6-amino-linker |
| | 3′ C6-amino-linker |
| | 5′ C12-amino-linker |
| | 3′ C12-amino-linker |
| | 5′-biotinylated C6-amino-linker |

METHOD FOR GENERATING A RNA-SEQUENCING LIBRARY

FIELD OF THE INVENTION

The invention refers to a novel method of preparing strand-specific RNA-sequencing libraries that can be used to identify DNA coding and non-coding strands that are transcribed to RNA. Such strand-specific RNA-sequencing libraries are especially useful in discovering anti-sense RNA and non-coding RNA. Random primer oligonucleotides, covalently coupled to a moiety, which blocks ligation, are used for RT reaction or the subsequent generation of the second DNA strand so that only one strand of the generated double-stranded DNA is ligated to sequencing adapters at the 5' nucleotide and sequenced by paired-end sequencing.

BACKGROUND OF THE INVENTION

In addition to mRNAs, which cover 1.5% of the genome in higher eukaryotes, numerous non-coding RNAs with widely varying expression levels have been identified. The biological function of these novel transcripts is largely unknown and represents a new research area, requiring high-throughput transcriptome studies to elucidate biological processes.

The high-throughput RNA sequencing (RNA-Seq) technology, enabled by the recent developments in next generation sequencing, has become a powerful tool in analyzing gene expression profiles, detecting transcript variants, and understanding the function of the non-coding regulatory RNAs. A standard RNA-Seq library is generated from ligating sequencing adapters to double-stranded DNA. There are two main classes of methods to prepare strand-specific RNA-Seq libraries. The first method comprises ligating different adapters to the 3' and 5' ends of the RNA molecules (see e.g. Ion Total RNA-Seq Kit v2 from Life Technologies). Another, more widely used method comprises incorporating dUTP in addition to dNTPs in the second strand DNA synthesis. Following adapter ligation, the second strand DNA can be specifically digested by an Uracil-N-glycosylase (UNG) enzyme so that only the library strand containing the first strand cDNA will be sequenced and information on the direction of the transcripts can therefore be obtained (see M. Sultan et al., Biochemical and Biophysical Research Communications 422 (2012) 643-646).

However, these conventional methods have their disadvantages.

The first method is subject to biased ligation of RNA, which is caused by structural properties within and between RNA substrates and the adapters used in ligation.

The more widely used method, which applies dUTP in addition to dNTPs in the second strand DNA synthesis, requires an additional UNG digestion step that follows the adapter ligation, making the library construction process more complicated and time-consuming. Additionally, just like any enzymatic reaction, the UNG reaction is not 100% efficient. Residual second strand cDNA may remain even after UNG digestion that can cause false interpretation of the RNA-sequencing data.

Thus, there is a need in the art for simpler and more specific methods for RNA sequence analysis.

SUMMARY OF THE INVENTION

The information on the exact strand from which the RNA is transcribed is useful in discovering the anti-sense and non-coding RNA species and studying their functions. The ability to distinguish the sense transcripts from the overlapping anti-sense transcripts can also further improve the accuracy of RNA quantification. In this context, we have developed a new RNA sequencing method, which is highly specific to amplifying a single-stranded template as well as a multiplicity of such strands and which, in contrast to the currently most widely-used RNA sequencing method as mentioned above, is highly specific without an additional enzymatic step to achieve amplification of a single sequencing template.

In particular, the invention refers to a method of RNA sequencing, whereby said method comprises:

(i) providing RNA;

(ii) generating (a) single-stranded first DNA strand(s) (cDNA), which is/are complementary to the RNA, by subjecting the RNA to reverse transcription by using a reverse transcriptase, a first set of oligonucleotide primers, and the RNA of step (i), and (iii) generating a second DNA strand by using a DNA polymerase, a second set of oligonucleotide primers, and the single-stranded cDNA of (ii), wherein a) the first set of oligonucleotide primers comprises a covalently coupled moiety at its/their 5' terminal nucleotide, which blocks ligation at the 5' terminus of the generated first DNA strand; or b) the second set of oligonucleotide primers comprises a covalently coupled moiety at its/their 5' terminal nucleotide, which blocks ligation at the 5' terminus of the generated second DNA strand.

In some embodiments, the method further comprises the subsequent steps of:

(iv) optionally end-repairing the double-stranded DNA strands using a polynucleotide kinase and an enzyme with polymerase and exonuclease activities to obtain end-repaired DNA strands;

(v) optionally adding a terminal adenine to the 3' termini of the DNA strands using a deoxynucleotidyl transferase enzyme; and (vi) ligation of adapters, which optionally comprise terminal thymines, to the DNA strands, which optionally comprise 3' terminal adenines.

Said methods may further comprise sequence analysis of the generated DNA.

In some embodiments, said method comprises:

(i) providing RNA;

(ii) generating (a) single-stranded first DNA strand(s) (cDNA), which is/are complementary to the RNA, by subjecting the RNA to reverse transcription by using a reverse transcriptase, a first set of oligonucleotide primers, and the RNA of step (i);

(iii) generating a second DNA strand by using a DNA polymerase, a second set of oligonucleotide primers, and the single-stranded cDNA of (ii);

(iv) ligating adapters to the double-stranded DNA; of step (iii) and (v) sequencing the generated DNA, wherein a) the first set of oligonucleotide primers comprises a covalently coupled moiety at its/their 5' terminal nucleotide, which blocks ligation at the 5' terminus of the generated first DNA strand; or b) the second set of oligonucleotide primers comprises a covalently coupled moiety at its/their 5' terminal nucleotide, which blocks ligation at the 5' terminus of the generated second DNA strand.

By generating the second DNA strand, a double-stranded DNA is generated.

In some embodiments of the above-mentioned method, prior to step (iv), the method comprises the step of:

(iii)(a) end-repairing the double-stranded DNA strands using a polynucleotide kinase and an enzyme with polymerase and exonuclease activities to obtain end-repaired DNA strands.

In some embodiments, step (iii)(a) is followed by step (iii)(b) comprising adding a terminal adenine to the 3' termini of the DNA strands by using a deoxynucleotidyl transferase enzyme, wherein the adapters comprise 3' terminal thymines, which in step (iv) ligate to the DNA strands comprising 3' terminal adenines.

In some embodiments, the oligonucleotide primers, which are covalently coupled to a blocking moiety and/or unmodified oligonucleotide primers, are random oligonucleotide primers.

In some embodiments, said methods comprise the initial step of extracting and optionally enriching the RNA of interest. In some embodiments, the extracted RNA is fragmented to an average size of 19-510 bp.

In some embodiments of the above methods, the molecules may be attached to a solid support for paired-end sequencing.

Another aspect of the invention refers to a kit, whereby said kit comprises:

(i) oligonucleotide primers comprising a moiety covalently coupled to the 5' terminal nucleotide, which blocks the ligation of the DNA to sequencing adapters;
(ii) unmodified oligonucleotide primers;
(iii) a reverse transcriptase; and
(iv) optionally, a DNA polymerase.

In some embodiments, the kit comprises:

(i) oligonucleotide primers comprising a moiety covalently coupled to the 5' terminal nucleotide, which blocks the ligation of the DNA to sequencing adapters;
(ii) unmodified oligonucleotide primers;
(iii) a reverse transcriptase;
(iv) optionally a DNA polymerase;
(v) a polynucleotide kinase and an enzyme with polymerase and exonuclease activities;
(vi) optionally a deoxynucleotidyl transferase enzyme;
(vii) two adapters, which optionally comprise a terminal thymine, each of which is complementary to a surface-bound amplification primer, respectively; and
(viii) a ligase.

In some embodiments of the above kit, the oligonucleotide primers, which are covalently coupled to a blocking moiety or unmodified oligonucleotide primers, are random oligonucleotide primers.

In some embodiments of the above methods or kits, the reverse transcriptase is selected from any one of retroviral reverse transcriptase, retrotransposon reverse transcriptase, hepatitis B reverse transcriptase, cauliflower mosaic virus reverse transcriptase, murine leukemia virus reverse transcriptase, avian myeoloblastosis virus (AMV), bacterial reverse transcriptase, Tth DNA polymerase, Taq DNA polymerase, Tne DNA polymerase, Tma DNA polymerase and enzymatically active mutants, fragments, variants and/or derivatives thereof.

In some embodiments a “moiety, which blocks ligation”, or a “blocking moiety” refers to a specific part of a larger molecule, which is more than one atom, herein the part of a modified oligonucleotide, which is covalently coupled to the 5' nucleotide of a modified primer oligonucleotide. Said moiety preferably blocks any ligation at the site, where the moiety is located, preferably at the 5' terminal nucleotide of the 5' terminus of an oligonucleotide.

In some embodiments of the above methods or kits, the oligonucleotide primer comprising a blocking moiety is characterized in that (i) the oligonucleotide comprises at the 5' terminal nucleotide a 5' phosphate that is not free, wherein optionally a 5' OH group or a 5' phosphate group at the 5' terminal nucleotide is covalently coupled to the moiety, which blocks ligation;
(ii) the base of the 5' terminal nucleotide is not any one of thymine, adenine, cytosine, guanine and uracil;
(iii) one or both 2' hydrogen(s) of the deoxyribose of the 5' terminal nucleotide is/are replaced by another atom or a blocking moiety; and/or
(iv) the oligonucleotide comprises a 5' terminal nucleotide having a pentose in a sterical conformation, which is not the sterical conformation of ribose or deoxyribose in RNA or DNA.

The ribose or deoxyribose conformation in RNA or DNA comprises or consists of the β-D-ribofuranose or β-D-deoxyribofuranose stereochemical conformation.

In some embodiments, in the phosphate, which is not free, one or more OH groups of the phosphate are modified in a way, such that the phosphate group may not be capable of undergoing a ligation reaction with a further mono-, oligo, or polynucleotide.

In some embodiments of the above methods or kits, the oligonucleotide primers comprising a covalently coupled moiety, which blocks ligation, comprise a 5' OH or a free 5' phosphate group at the 5' terminal nucleotide before being covalently coupled to a moiety, which confers the property of ligation-blocking.

In some embodiments of the above methods or kits, the 5' phosphate group of the deoxyribose of the 5' terminal nucleotide of the oligonucleotide primer comprising a covalently coupled moiety, which blocks ligation, is esterified, or the 5' OH group of the 5' terminal nucleotide of the oligonucleotide primer comprising a covalently coupled moiety, which blocks ligation, is esterified or etherified.

In some embodiments of the above methods or kits, the 5' phosphate group of the oligonucleotide primer comprising a covalently coupled moiety, which blocks ligation, is esterified by an alkyl or aryl alcohol, or the 5' OH group of the oligonucleotide primer comprising a covalently coupled moiety, which blocks ligation, is esterified by a monoalkyl phosphate, dialkyl phosphate, monoalkyl- or dialkyl phosphothionate, or by a boronic acid.

In some embodiments of the above methods or kits, the alkyl or aryl alcohol comprises at least one additional functional group, which is selected from a mono- or polyether, mono- or polyester, carboxylate, primary amine or hydroxyl groups, or the monoalkyl phosphate, dialkyl phosphate, monoalkyl or dialkyl phosphothionate, or boronic acid comprises at least one additional functional group, which is selected from mono- or polyether, mono- or polyester, carboxylate, primary amine or hydroxyl groups.

In some embodiments of the above methods or kits, the 5' OH group of the deoxyribose of the 5' terminal nucleotide of the oligonucleotide primer comprising a covalently coupled moiety, which blocks ligation, is esterified by a molecule selected from 5'-spacers such as 5' Spacer 18, 5' Spacer 9, 5' C3-Spacer, 5' C6-Spacer, 5' abasic residues (d spacer, r spacer), 5'-5' inverted nucleotides, and 5' linkers, such as DADE-linker, 5' C6-amino-linker, 5' C12-amino-linker, and 5'-biotinylated 5' C6 or 5' C12-amino-linker.

A subset of agents/moieties for covalent coupling to 5'OH group is disclosed in FIG. 5.

In some embodiments of the above methods or kits, an unmodified 5' terminal nucleotide is covalently coupled to any one of fludarabine, azathioprine, mercaptopurine, pentostatin, cladribine, floxuridine, gemcitabine, cytarabine, gemcitabine, capecitabine, and tegafur.

In some embodiments of the above methods or kits, the generated first DNA strand, which comprises a moiety, which blocks ligation at the 5' terminus, further comprises at its 3' terminus a covalently coupled moiety, which blocks ligation at said 3' terminus and which is introduced after the generation of the first DNA strand.

In some embodiments, the 3' OH group of the 3' terminus of the first DNA strand is not free, preferably wherein said 3' OH group is covalently coupled to a moiety, which blocks ligation. Even more preferably, said covalent coupling to a moiety, which blocks ligation, is an esterification or an etherification of the 3' OH group of the 3' terminus of the first DNA strand.

In some embodiments of the above methods or kits, the adapters hybridize with two different surface-bound amplification primers.

BRIEF DESCRIPTION OF THE DRAWINGS

FIG. 3 shows the percentage of either first (R1) or the second (R2) reads, which belong to the forward (i.e. the DNA, which is generated second) or reverse strand (i.e. the DNA strand, which is generated first) of the reference or the sample comprising oligonucleotides, which are covalently coupled to a blocking moiety. MOD R1 refers to the percentage of the reads that are mapped to the forward, or coding, strand of the reference sequences (known non-overlapping coding RNA). MOD R2 refers to the percentage of the reads that are mapped to the reverse (non-coding) strand of the reference sequences (known non-overlapping coding RNA). In the ideal situation, 100% reads should be mapped to the forward strand. The small percentage of the reads still mapped to the reverse strands can be caused by incompleteness of the reference sequences and/or genomic DNA contamination.

DETAILED DESCRIPTION OF THE INVENTION

Definitions

Figure 1:
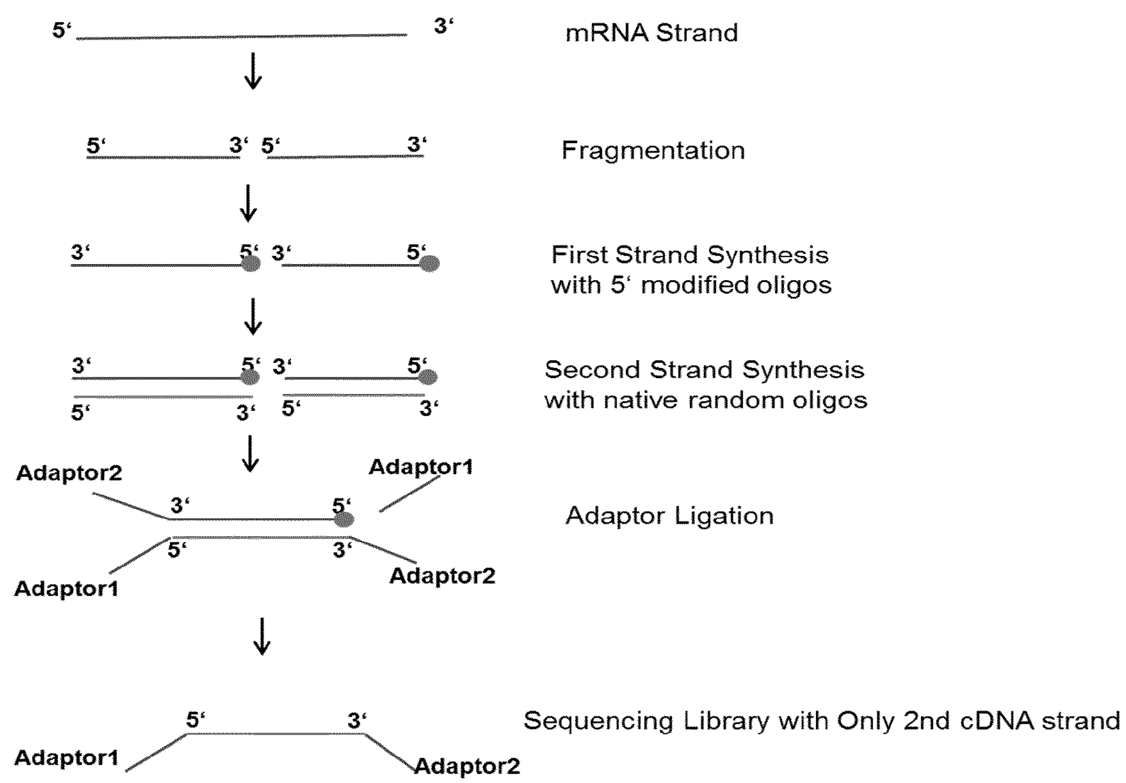
FIG. 1: Workflow for the RNA-Seq Library preparation, which comprises the use of oligonucleotides, which are covalently coupled to a blocking moiety have a 5' C3 spacer at the 5' terminus. Such a spacer inhibits the ligation of generated dsDNA with sequencing adapters.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry).

In practicing the present invention, many conventional techniques in molecular biology, microbiology, and recombinant DNA may be used. These techniques are well-known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods In Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

The term "library" refers to a large number of nucleic acid fragments, here a collection of DNA fragments for sequencing analysis, which are generated from RNA. The libraries referred to herein are generated by fragmentation of a sample to be analyzed, reverse-transcription and generation of dsDNA, optional end-repairing, optional addition of a terminal adenine, and ligation of strands generated from fragments and adapters when the ligation is not inhibited by a random oligonucleotide, which is covalently coupled to a blocking moiety. Optionally, the purified DNA fragments are amplified and/or enriched before they are sequenced.

As used herein, the term "about" when used together with a numerical value (e.g. a temperature or time specification) is intended to encompass a deviation of 20%, preferably 10%, more preferably 5%, even more preferably of 2%, and most preferably of 1% from that value. When used together with a numerical value it is at the same time to be understood as individually disclosing that exact numerical value as a preferred embodiment in accordance with the present invention.

As used herein, the term "comprising" is to be construed as encompassing both "including" and "consisting of", both meanings being specifically intended, and hence individually disclosed embodiments in accordance with the present invention.

"RNA" refers to both a single RNA strand and to a multiplicity of RNA strands. Accordingly, "DNA" refers to both a single-stranded DNA or double-stranded DNA strand and to a multiplicity of such DNA strands.

"nt" is an abbreviation of "nucleotide".

"bp" is an abbreviation of "base pair".

The term "template" as used herein refers to a double-stranded or single-stranded nucleic acid molecule which is to be used for the generation of a first (single-stranded) DNA strand (cDNA) or a second DNA strand, thereby generating double-stranded DNA, which is to be amplified, copied or sequenced. An oligonucleotide primer, complementary to a portion of a nucleic acid template, preferably an RNA molecule, is hybridized under appropriate conditions, and the reverse transcriptase of the invention may then synthesize a DNA molecule complementary to said template or a portion thereof.

Further, an oligonucleotide primer, complementary to a portion of a nucleic acid template, preferably the first cDNA strand, is hybridized under appropriate conditions, and the DNA polymerase I of the invention may then synthesize a DNA molecule complementary to said template or a portion thereof. The appropriate conditions preferably are high stringency conditions.

Preferably, such a random oligonucleotide primer hybridizes with the template RNA or DNA under high stringency conditions; even more preferably, the random oligonucleotide primer is complementary to the template DNA or RNA. Such oligonucleotides have a length of 6-10 nucleotides, preferably of 6 nucleotides.

Under "high stringency" (for example: high temperature and/or low salt concentration), only exact matches of bases will anneal and stay together. To achieve high stringency in the amplification techniques described herein, e.g. PCR, the annealing temperature of the primers/probes is usually about 5° C. less than the melting temperature, ensuring that only their desired target strand is generated or amplified.

"Oligonucleotide" refers to a synthetic or natural molecule comprising a covalently linked sequence of nucleotides in the range of 2 to approximately 20 nucleotides, which are joined by a phosphodiester bond between the 3' position of the pentose of one nucleotide and the 5' position of the pentose of the adjacent nucleotide. Preferably, the pentose is a deoxyribose.

Random oligonucleotide refers to oligonucleotide(s), which is/are synthesized entirely randomly to give a numerous range of sequences that have the potential to anneal at many random points on a DNA sequence and act as (a) primer/primers to commence first strand cDNA and/or second strand DNA synthesis.

"Unmodified oligonucleotides" as used herein refer to any oligonucleotides, which may be generated for amplification purposes of DNA or the generation of cDNA when subjecting an RNA template to reverse transcription. Preferably, the unmodified oligonucleotides, which are applied for RNA sequencing purposes, are 5' phosphorylated at their 5' terminal nucleotides. Such oligonucleotides do not comprise a moiety, which blocks ligation to a further mono-, oligo-, or polynucleotide.

"Polynucleotide" refers to a synthetic or natural molecule comprising a covalently linked sequence of nucleotides in the range of approximately 20 or more nucleotides, which are joined by a phosphodiester bond between the 3' position of the pentose of one nucleotide and the 5' position of the pentose of the adjacent nucleotide. Preferably, the pentose is a deoxyribose.

"T4 Polynucleotide Kinase" refers to an enzyme that catalyzes the transfer and exchange of $P_i$ from the γ position of ATP to the 5'-hydroxyl terminus of polynucleotides (double- and single-stranded DNA and RNA) and nucleoside 3'-monophosphates.

"T4 DNA Polymerase" refers to an enzyme that catalyzes the synthesis of DNA in the 5'→3' direction and requires the presence of a template and a primer. This enzyme has a 3'→5' exonuclease activity which is much more active than that found in DNA Polymerase I (*E. coli*). T4 DNA Polymerase does not exhibit 5'→3' exonuclease activity.

"Klenow fragment exo-" or "Klenow fragment (3'→5' exo-)" refers to an N-terminal truncation of DNA Polymerase I which retains polymerase activity, but has lost the 5'→3' exonuclease activity and the 3'→5' exonuclease activity.

"T4 DNA Ligase" refers to an enzyme that catalyzes the formation of a phosphodiester bond between juxtaposed 5' phosphate and 3' hydroxyl termini in double-stranded DNA or RNA. This enzyme joins both blunt end and cohesive (sticky) ends.

"T3 DNA ligase" refers to an ATP-dependent dsDNA ligase from bacteriophage T3. It catalyzes the formation of a phosphodiester bond between adjacent 5' phosphate and 3' hydroxyl groups of duplex DNA. The enzyme joins both cohesive (sticky) and blunt ends.

"T7 DNA Ligase" is an ATP-dependent ligase from bacteriophage T7. This enzyme joins cohesive (sticky) ends and it is suitable for nick sealing. Blunt-end ligation does not occur in the presence of T7 ligase.

"T4 RNA Ligase" is an ATP-dependent enzyme that catalyzes the ligation of a 5' phosphoryl-terminated nucleic acid donor to a 3' hydroxyl-terminated nucleic acid acceptor through the formation of a 3'→5' phosphodiester bond, whereby ATP is hydrolyzed to AMP and $PP_i$. Substrates include single-stranded RNA and DNA as well as dinucleoside pyrophosphate.

The term "RNA" in the present invention relates to any one of viral RNA, prokaryotic RNA, archaeal RNA, or eukaryotic RNA. cDNA may be obtained from any one of viral RNA, and RNA from prokaryotes, archaea, and eukaryotes by generating complementary DNA (cDNA) by conducting reverse transcription using a reverse transcriptase. Double-stranded DNA may be obtained by generating a complementary second strand to the single-stranded cDNA strand.

Enzymes in the methods and/or kits of the invention include any enzyme having reverse transcriptase activity. Such enzymes include, but are not limited to, retroviral reverse transcriptase, such as HIV, SIV, or HTLV, retrotransposon reverse transcriptase, hepatitis B virus reverse transcriptase, cauliflower mosaic virus reverse transcriptase, murine leukemia virus reverse transcriptase, avian myeoloblastosis virus (AMV), bacterial reverse transcriptase, Tth DNA polymerase, Taq DNA polymerase (Saiki, R. K., et al., Science 239:487-491 (1988); U.S. Pat. Nos. 4,889,818 and 4,965,188), Tne DNA polymerase (WO 96/10640), Tma DNA polymerase (U.S. Pat. No. 5,374,553) and mutants, fragments, variants or derivatives thereof (see, e.g., U.S. Pat. Nos. 5,948,614 and 6,015,668). Modified reverse transcriptases may be obtained by recombinant or genetic engineering techniques that are routine and well-known in the art. Mutant reverse transcriptases can, for example, be obtained by mutating the gene or genes encoding the reverse transcriptase of interest by site-directed or random mutagenesis. Such mutations may include point mutations, deletion mutations and insertional mutations.

"Oligonucleotides, which are covalently coupled to a blocking moiety" or "(ligation-)blocking oligonucleotides" as used herein refer to any oligonucleotides, which inhibit or block ligation of adapters to single-stranded- or double-stranded DNA, preferably dsDNA as described in the present invention. Specifically, the oligonucleotides comprise a moiety, which blocks ligation at the 5' terminal nucleotide of the 5' oligonucleotide primer.

In particular, the blocking moiety is covalently coupled to the 5' OH group of the 5' terminal pentose. In other embodiments, the blocking moiety is covalently coupled to the 5' phosphate group at the 5' terminal pentose.

A deoxyribose within a blocking moiety may be chemically modified in a way that the 5' phosphate is not free, i.e. one or more of the OH groups of the phosphate group within the moiety may not be capable of undergoing a ligation reaction with a further mono-, oligo-, or polynucleotide; the deoxynucleotide within a moiety may be chemically modified in a way that the base of the 5' terminal nucleotide is not any one of thymine, adenine, cytosine, guanine and uracil; the deoxynucleotide within a blocking moiety may be modified in a way that one or both 2' hydrogen(s) of the deoxyribose of the 5' terminal nucleotide is/are replaced by another atom or a blocking moiety; and/or the oligonucleotide comprises a 5' terminal nucleotide having a pentose in a sterical conformation, which is other than that of ribose or deoxyribose in unmodified RNA or DNA. The ribose or deoxyribose conformation in unmodified RNA or DNA comprises or consists of the β-D-ribofuranose or β-D-deoxyribofuranose stereochemical conformation.

The term "modification" or "modified" refers to any change of a mono-, oligonucleotide, or a polynucleotide, which renders the respective generated DNA strand unable to ligate.

The term "moiety" refers to a specific part of a larger molecule, which is more than one atom, herein the part of a ligation-blocking oligonucleotide, which is covalently coupled to the 5' nucleotide of a ligation-blocking primer oligonucleotide. Said moiety preferably blocks any ligation at the site, where the moiety is located, preferably at the 5' terminal nucleotide of the 5' terminus of an oligonucleotide.

A blocking moiety may be a covalently coupled molecule, which is coupled to the 5' phosphate or 5'OH group of the 5' terminal nucleotide, whereby said coupling in both cases may be achieved by an ester bond, preferably a diester bond. A subset of 5'OH group blocking moieties is disclosed in FIG. 5. Preferably, such blocking moieties include, but are not restricted to, any one of the following 5'-spacers such as 5' Spacer 18, 5' Spacer 9, 5' C3-Spacer, 5' C6-Spacer, 5' abasic residues (d spacer, r spacer), 5'-5' inverted nucleotides, and 5' linkers, such as DADE-linker, 5' C6-amino-linker, 5' C12-amino-linker, or 5'-biotinylated 5' C6 or 5' C12-amino-linker or any functional analog thereof.

"Free" 5' phosphate refers to a phosphate group, which is esterified with a 5' OH group of a 5' pentose of a 5' nucleotide only, preferably a deoxyribose of a terminal mono-, oligo-, or polynucleotide, preferably an oligonucleotide or a DNA strand, which was generated by using an oligonucleotide primer having a free 5' phosphate. Said phosphorylated 5' pentose is a monoester, which comprises two "free" OH groups, i.e. OH groups within the phosphate group, which may be subject to esterification with one or two compounds, which comprise at least one primary or secondary OH group. The (primer) oligonucleotides comprising such a free 5' phosphate are referred herein as unmodified oligonucleotides. A further esterification may be carried out inter alia, by ligation to a further mono-, oligo-, or polynucleotide, or by a blocking moiety of the invention.

A phosphate at the 5' terminal nucleotide, which is not free, refers to a phosphate, which is esterified with an alcohol group of a blocking moiety. For example, the alcohol (OH) group may be the 5'OH group of a 5' pentose, preferably a deoxyribose of a terminal nucleotide of a further DNA molecule, such as mono-, oligo-, or polynucleotide, which is additionally esterified at its 5' terminus. Such an "oligonucleotide comprising a ligation-blocking moiety" may be used to generate a DNA strand as a primer, which as a consequence also comprises a phosphate group, which is not free.

Figure 5:
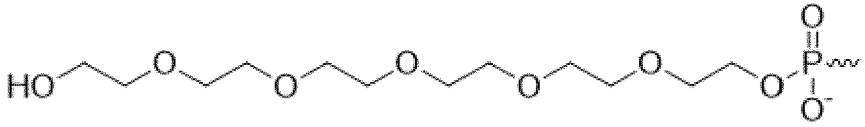
FIG. 5: Structural formula of a subset of suitable agents/moieties, which block ligation of oligonucleotide primers: Wavy line indicates the coupling by an ester bond to a nucleotide or an oligonucleotide at the 5' terminal OH group (index 5') or at the 3' terminal 3'OH group (index 3') of a primer nucleotide or an oligonucleotide, preferably a primer oligonucleotide.
Figure 5:
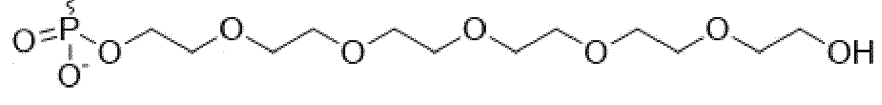
Figure 5:
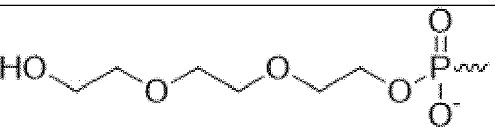
Figure 5:
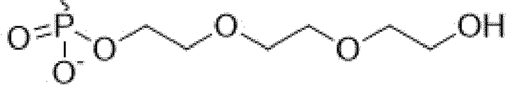
Figure 5:
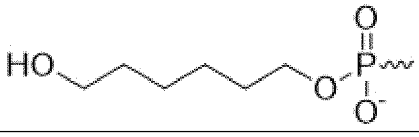
Figure 5:
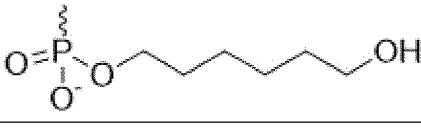
Figure 5:
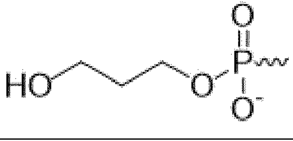
Figure 5:
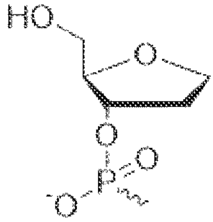
Figure 5:
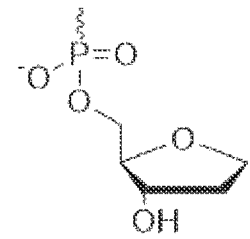
Figure 5:
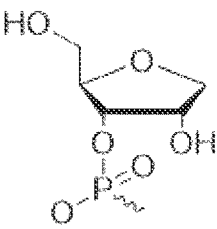
Figure 5:
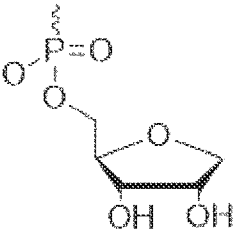
Figure 5:
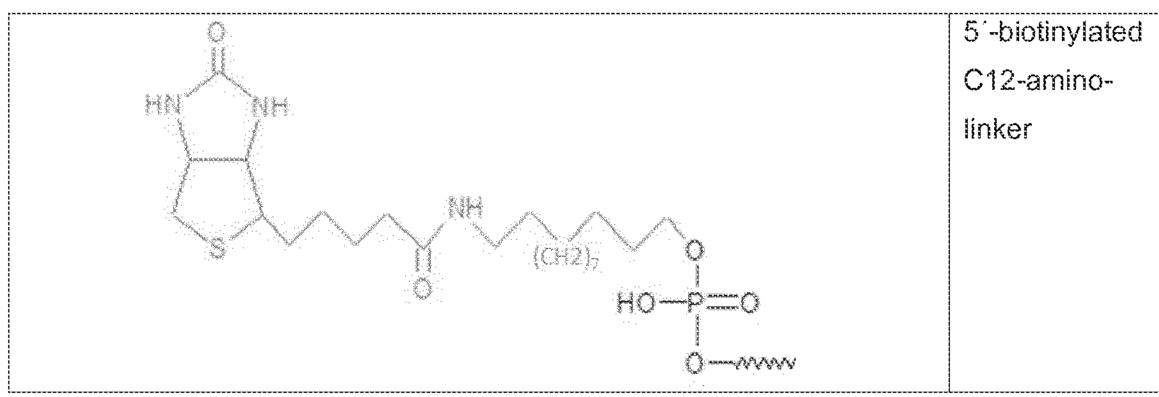

A subset of agents, which may be covalently coupled as moieties to an oligonucleotide strand at the 3'OH group of the 3' terminus, is disclosed in FIG. 5. Such agent molecules include, but are not restricted to any one of the following 3' Spacer 18, 3' Spacer 9, 3' C3-Spacer, 3' C6-Spacer, 3' abasic residues (d spacer, r spacer), 3' C6-amino-linker, and a 3' C12-amino-linker and any functional analog thereof.

The term "functional analog" or "analog" refers to a compound or a molecule, which has a similar structure to that of another one, but which differs from the other one by a certain component. It can differ in one or more atoms, functional groups, or substructures, which are replaced with other atoms, groups, or substructures. In addition, such an analog has similar physical, chemical, and/or biochemical properties.

The term "functional group" refers to specific groups (moieties) of atoms or bonds within molecules that may be responsible for the characteristic chemical reactions of those molecules.

Functional groups described herein are selected from, but not restricted to any one of mono- or poly-ether, mono- or polyester, carboxylate, primary amine, halogens, such as F, Cl, Br, or I, or hydroxyl groups.

The term "boronic acid" refers to an alkyl or an aryl substituted boric acid, which contains a carbon-boron bond and belongs to the larger class of organoboranes. They are capable of forming covalent complexes with e.g. sugars, amino acids or hydroxamic acids, such as an ester bond to the 5'OH group of the 5' nucleotide of an oligonucleotide.

The term "thiophosphate" refers to compounds, which comprise a $PS_{4-x}O_x^{3-}$ (with x=0, 1, 2, or 3) instead of a phosphate group. The features of phosphates referred herein with regard to chemical properties and chemical modifications, such as coupling by esterification, analogously apply to thiophosphates.

The term "spacer" refers to moieties, which are used for incorporating a long artificial arm into an oligonucleotide, thereby allowing for e.g. solid-phase immobilization of hybridization probes, and inhibiting ligation of resulting dsDNA to other DNA, such as sequencing adapters. Such spacer moieties include, but are not limited to ribonucleotides, deoxyribonucleotides, or any analogs thereof, which may be chemically modified.

The term "fragment" refers to any RNA sequence isolated from a virus, prokaryote, eukaryote, or archaeum, and which has been generated by fragmentation by means known to the skilled person, such as heating. Preferably, fragments for RNA sequencing have a length of 19-510 bp, preferably, 60-450 bp, more preferably 70-420 bp, even more preferably 100-350 bp, and most preferably 100-200 bp.

The term "RNA" refers to "long RNA molecules" that are at least 200 nt in length or "short RNA molecules" that are less than 200 nt in length. Long RNA molecules include mRNA molecules, rRNA molecules and long non-coding RNA molecules such as large intergenic RNA (lincRNA) molecules. Short RNA molecules include tRNA molecules and a variety of small non-coding regulatory RNAs generically referred herein to as "small RNAs", i.e, short interfering RNAs (siRNAs), microRNAs (miRNAs), tiny non-coding RNAs (tncRNAs) and small modulatory RNAs (smRNAs).

As used herein, the term "adapter" refers to an oligonucleotide, which is able to ligate DNA or RNA. An adapter may be, e.g., an RNA adapter, a DNA adapter, or it may be composed of both ribonucleotides and deoxyribonucleotides, or analogs thereof. An adapter may be labeled or unlabeled. The adapter sequence has a length of about 30-80 bases, preferably about 30-70 bases, even more preferably, 60-70 bases or 30-40 bases. In some even more preferred embodiments, the adapter length is about 62 bases or 30-40 bases. The adapters may be blunt-ended or they may have sticky ends. Preferably, the adapters have cohesive ends and comprise 3' thymines.

Methods

One aspect of the invention refers to methods for RNA sequencing, in particular in the context of generating RNA libraries, whereby the methods are discussed below in more detail.

Some embodiments of the methods described herein involve fragmenting an initial sample of RNA that contains intact long RNA and intact short RNA to obtain a fragmented RNA sample. The long RNA in the initial sample is at least 200 nucleotides and may e.g. include cellular mRNA, long non-coding RNAs (such as lincRNA) and/or rRNA. The defining characteristics of mRNA and rRNA are well known. lincRNA has been recently discovered, and is believed to be involved in regulating a wide variety of processes, e.g, embryonic stem cell pluripotency, cell proliferation, cancer and chromatin structure, see Tingeras (Nature Biotechnology 2009 27: 346-347). The short RNA in the initial sample is less than 200 nucleotides in length and may include tRNA and a variety of small non-coding regulatory RNAs generically referred herein to as "small RNAs", i.e, short interfering RNAs, microRNAs, tiny non-coding RNAs and small modulatory RNAs. Small RNAs are a group of non-coding regulatory RNAs that have defined sequences and that are in the range of 18-29 nucleotides (nts) in length. Many small RNAs are approximately 19-25 bp in length.

Novina et al. (Nature 2004 430:161-164) classify small RNAs into at least four groups: a) short interfering RNAs (siRNAs), b) micro-RNAs (miRNAs), c) tiny non-coding RNAs (tncRNAs) and d) small modulator RNAs (smRNAs). siRNAs are a class of double stranded RNAs of approximately 21-22 nt in length, generated from double stranded RNAs. siRNAs are thought to silence gene expression by promoting the cleavage of mRNAs. miRNAs, on the other hand, are a class of single stranded RNAs of approximately 19-25 nt in length. miRNAs appear to be evolutionary conserved and are thought to silence gene expression by inhibiting translation. tncRNAs are a class of RNAs that are about 20-22 nucleotides. tncRNAs appear to be developmentally regulated, although their function is unknown. smRNAs are double stranded RNAs involved in regulating neuron-specific gene expression in adult neurons.

The initial RNA sample may contain, for example, total cellular RNA or RNA that has been enriched or depleted for one or more types of RNA, such as rRNA and/or tRNA, mRNA small RNA, long non-coding RNA, and small RNA.

Methods for fragmenting RNA for e.g. sequencing purposes include chemical, enzymatic or thermal fragmentation methods, for which protocols are known (see, e.g., Chandler et al., Appl. Environ. Microbiol. 2003 69:2950-2958, Guschin et al. Appl. Environ. Microbiol. 1997 63:2397-2402; Kelly et al., Anal. Biochem. 2002 311:103-118, Liu et al. Environ. Microbiol. 2001 3:619-629, Mehlmann et al., Anal. Biochem. 2005 347:316-323, Nguyen Nucleic Acids Res. 2000 28:3904-3909, Proudnikov Nucleic Acids Res. 2006 24:4535-4542, Small et al., Appl. Environ. Microbiol. 2001 67:4708-4716).

In some embodiments, the intact RNA may be fragmented using basic conditions, e.g., incubation in NaOH (e.g. 50 mM NaOH) at an elevated temperature (e.g., 55° C.) for a period of time (e.g., 10-30 minutes), as described in Liu et al. (Applied and Environmental Microbiology, 2007 73: 73-82). In other embodiments, the fragmentation may be metal ion catalyzed in that the intact RNA may be incubated with a metal ion, e.g, an ion of the lanthanide series or a divalent metal ion such as $Mg^{2+}$ or $Zn^{2+}$ (which may be at a concentration of, e.g., 5 mM to 200 mM) at an elevated temperature (e.g, in the range of 50° C. to 95° C.) for a period of time, e.g., 1 minute to 1 hour, as described in, e.g. Brown et al. (J. Am. Chem. Soc. 2002 124: 7950-7962). For example, RNA may be fragmented by incubation with 10 mM of zinc sulfate ($ZnSO_4$) or zinc chloride ($ZnCl_2$) in 25 mM of Tris-HCl (pH 7.4) at 60° C. for 30 min, as described by Liu, see above.

In some embodiments, the RNA may be incubated with 10 mM $ZnCl_2$ in 10 mM Tris-HCl pH 7 for 15 minutes at 70° C. to produce fragments of 60 to 200 bases in length. In some embodiments, the RNA in 40 mM Tris-acetate pH 8.1, 100 mM KOAc and 30 mM MgOAc for 20-30 min at 75° C. Fragments that are generally between 38 and 150 bases in length are obtained, as described by Mehlmann et al. (Analytical Biochemistry 2005 347: 316-323).

All of the incubation periods described above may be altered to increase or decrease the lengths of the fragments that are obtained, as desired. Fragment sizes for RNA sequencing are about 19-510 bp, preferably about 60-450 bp, more preferably about 70-420 bp, even more preferably about 100-350 bp, and most preferably about 100-200 bp.

Since fragmentation using the above methods occurs non-specifically at approximately random positions throughout the RNA, the fragmentation on average occurs in longer RNAs on a per molecule basis, because the longer RNA molecules contain more potential sites for fragmentation to occur. For example, fragmentation conditions that fragment RNA to fragments of 60 to 200 bases in length should, on average, fragment an RNA molecule of 3 kb in length at approximately 15 to 50 sites without fragmenting a small RNA of approximately 18-30 nucleotides in length. Fragmentation of an RNA sample that contains long RNA molecules and short RNA molecules therefore results in a fragmented sample that contains: a) fragments of long RNA molecules and b) short RNA molecules which are largely intact. The fragmentation may hence be carried out in the presence of oligonucleotides, which are short enough not to be fragmented during the fragmentation process.

In some embodiments, the first (single-stranded) DNA strand (cDNA) is generated by using a reverse transcriptase (RT), which comprises using RNA or fragmented RNA as template(s) and by using oligonucleotide primers, which hybridize with RNA. In some embodiments, these, preferably random, oligonucleotides are covalently coupled to a blocking moiety. The reverse transcriptase for the generation of the complementary DNA (cDNA) strand comprises any reverse transcriptase known to the skilled person or any functional derivative thereof, and it includes, but is not restricted to retroviral reverse transcriptase, retrotransposon reverse transcriptase, hepatitis B reverse transcriptase, cauliflower mosaic virus reverse transcriptase, murine leukemia virus reverse transcriptase, avian myeoloblastosis virus (AMV), bacterial reverse transcriptase, Tth DNA polymerase, Taq DNA polymerase, Tne DNA polymerase, Tma DNA polymerase or enzymatically active mutants, fragments, variants or derivatives thereof.

In some embodiments, the reverse transcriptase is a qScript Reverse Transcriptase (Quanta BioSciences). In preferred embodiments, the reverse transcriptase reaction is carried out at 25° C. for about 10 minutes, followed by incubation at 42° C. for about 50 minutes. Inactivation of the reverse transcriptase enzyme is carried out at 70° C. for about 15 minutes.

In some embodiments, the reverse transcription reaction is followed by a purification step, before the cDNA is subjected to the synthesis of a second DNA strand, whereby a double-stranded DNA is generated. Such purification is carried out by using e.g. the QIAquick Nucleotide Removal Kit (QIAGEN). By applying such a kit, unincorporated nucleotides, salts, and other contaminants are removed and oligonucleotides (>17 nt) and DNA fragments ranging from 40 bp to 10 kb are purified using a simple and fast bind-wash-elute procedure and an elution volume of about 30-200 μl.

In some embodiments, the second DNA strand is generated by using a DNA Polymerase I by applying oligonucleotides as primers, which hybridize with the first cDNA strand for the sequence generation. In some embodiments, these preferably random oligonucleotides are covalently coupled to a blocking moiety. Preferable conditions for generating such (a) second strand(s) are 25° C. for about 30 minutes.

In some embodiments, the subsequent step of end-repairing of DNA generated from fragmented RNA may be carried out after completion of generating the second DNA strand. In other embodiments, the end-repairing step is carried out simultaneously with the generation of the second strand. The end-repair step requires at least two enzymes: (a) a polynucleotide kinase, preferably the T4 Polynucleotide Kinase (PNK) that phosphorylates the 5'-terminus of the double stranded DNA fragments; and (b) an enzyme or enzymes with polymerase and exonuclease activities that make the ends of the DNA fragments blunt by either fill-in or trimming reactions, such as e.g. T4 DNA Polymerase. Preferably, DNA Polymerase I, the polynucleotide kinase, and the enzyme with polymerase and exonuclease activities are all inactivated for about 10 minutes at about 70° C.

In some embodiments, the oligonucleotides used in the generation of the first single-stranded DNA strand (cDNA) are oligonucleotides, preferably random modified oligonucleotides comprising a covalently coupled blocking moiety. In other embodiments, the oligonucleotides in the generation step of the second DNA strand are oligonucleotides, preferably random modified oligonucleotides comprising a covalently coupled blocking moiety. The generation of the second DNA strand results in double-stranded DNA, whereby the second DNA strand comprises a blocking moiety, which preferably is coupled to the oligonucleotide. The oligonucleotides comprising a blocking moiety include, but are not restricted to 6mer-10mer random oligonucleotides, preferably, random 6mer oligonucleotides. Preferably, these oligonucleotides are covalently coupled to a moiety in a way as to block a ligation reaction at the 5' terminal nucleotide. More preferably, the ligation reaction to subsequent sequencing adapters is blocked. More specifically, these oligonucleotides do not possess a free 5' phosphate group at their 5' end, the base of the 5' terminal oligonucleotide is not any one of thymine, adenine, cytosine, guanine and uracil; one or both 2' hydrogens of the deoxyribose of the 5' terminal nucleotide is/are replaced by another atom or a blocking moiety and/or the oligonucleotide comprises a 5' terminal nucleotide having a pentose in a sterical conformation, which is other than that of ribose or deoxyribose in RNA or DNA. Preferably, such pentose molecules include but are not restricted to arabinose.

In preferred embodiments, the unmodified oligonucleotide primers referred to herein are phosphorylated at their 5' termini.

In some embodiments, the oligonucleotide primers comprising a covalently coupled moiety, which blocks ligation, comprise a 5' OH or a free 5' phosphate group at the 5' terminal nucleotide before being covalently coupled to a blocking moiety.

In some embodiments, oligonucleotides comprising a covalently coupled blocking moiety or unmodified oligonucleotides hybridize under high stringency conditions. More preferably, the oligonucleotides are complementary to the template DNA or RNA.

In preferred embodiments, the oligonucleotide primers comprising a covalently coupled moiety, which blocks ligation, comprise a 5' OH at the 5' terminal nucleotide of an oligonucleotide primer, which is covalently coupled to a blocking moiety. In other embodiments, the oligonucleotide primers comprising a covalently coupled moiety, which blocks ligation, comprise a 5' phosphate group at the 5' terminal nucleotide, which is covalently coupled to a blocking moiety.

In some embodiments, the 5' phosphate group of the 5' nucleotide of the oligonucleotide primer comprising a covalently coupled moiety, which blocks ligation, is esterified by a diester bond between the phosphate group of the pentose, preferably deoxyribose of the 5' terminal nucleotide of the oligonucleotide primer and a hydroxyl (OH) group of a hydrocarbon comprising at least one OH group, preferably an aryl or alkyl alcohol, which comprises at least one OH group, more preferably a primary or a secondary alkyl alcohol or the OH group of an 5'5' inverted nucleotide. In other embodiments, the 5'OH group of the oligonucleotide primer comprising a moiety, which blocks ligation, is esterified or etherified, preferably by an acidic group, more preferably by a monoalkyl phosphate, dialkyl phosphate, monoalkyl- or dialkyl phosphothionate, or by a boronic acid.

The alkyl or aryl alcohol, preferably primary or secondary alkyl alcohol may further comprise at least one additional functional group. Preferably, such a functional group is selected from, but not restricted to a mono- or poly-ether, mono- or polyester, carboxylate, primary amine or hydroxyl groups. The alkyl or aryl alcohol may comprise cyclic ethers, such as 2-methyl-tetrahydrofuran and its derivatives. In some embodiments, the monoalkyl or aryl alcohol, preferably primary or secondary alcohol, comprises a biotinyl group.

In some embodiments, the monoalkyl phosphate, dialkyl phosphate, monoalkyl or dialkyl phosphothionate or boronic acid comprises at least one additional functional group, which is selected from any one of the following: mono- or polyether, mono- or polyester, carboxylate, primary amine or hydroxyl groups. In preferred embodiments, the 5'OH group of the 5' nucleotide is esterified by molecules including, but not limited to, 5'-spacers such as 5' Spacer 18, 5' Spacer 9, 5' C3-Spacer, C6-Spacer, 5' abasic residues (d spacer, r spacer), 5'-5' inverted nucleotides, and 5' linkers DADE-linker, 5' C6-amino-linker, 5' C12-amino-linker, or biotinylated 5' C6-amino-linker5' C12-amino-linker, or any functional analog thereof.

In some embodiments, the generated first single-stranded DNA strand, which comprises a moiety, which blocks ligation (a blocking moiety covalently coupled to the strand), at the 5' terminus of the 5' terminal nucleotide, may further comprise a further moiety at the 3' terminus, which blocks ligation (a blocking moiety covalently coupled to the strand). Said covalent coupling of a blocking moiety is introduced after the generation of the first DNA strand. Preferably, the 3' OH group of the 3' terminus of the first DNA strand is not free, preferably wherein said 3' OH group is covalently coupled to a blocking moiety.

In some embodiments, an unmodified 5' terminal nucleotide is covalently coupled to any one of fludarabine, azathioprine, mercaptopurine, pentostatin, cladribine, floxuridine, gemcitabine, cytarabine, gemcitabine, capecitabine, and tegafur.

In some embodiments, one or both 2' hydrogen(s) of the 5' nucleotide of the 5' terminus of an oligonucleotide is/are replaced by an atom or a blocking moiety selected from, but not restricted to a halogen atom, preferably, F, Cl, Br, or I, or a C1-C5 alkyl or C1-C5 alkoxy group, preferably C1-C3 alkyl or C1-C3 alkoxy group, which may or may not comprise one or more additional functional groups.

In some embodiments, the 3' OH group at the 3' end/terminus of the oligonucleotide comprises a covalently coupled blocking moiety. In some embodiments, the modification consists of a dideoxynucleotide, or an oligonucleotide comprising a 3' terminal dideoxynucleotide.

In some embodiments, the 3'OH group of the pentose of the 3' terminal nucleotide, preferably deoxyribose of the 3' terminal nucleotide of the generated first strand is additionally esterified by a monoalkyl or dialkyl phosphate. In other embodiments, the 3'OH group of the pentose, preferably deoxyribose of the 3' terminal nucleotide of the generated first strand may be esterified by phosphothionate. In yet other embodiments, the 3'OH group of the pentose, preferably deoxyribose of the 3' terminal nucleotide of the oligonucleotide is esterified by a boronic acid. The mono- or dialkyl phosphate, alkyl phosphothionate or boronic acid preferably comprises at least one additional functional group. Preferably such a functional group is selected from, but not restricted to a mono- or polyether, mono- or polyester, carboxylate, primary amine or hydroxyl groups. The monoalkyl phosphate may comprise cyclic ethers, such as 2-methyl-tetrahydrofuran and its derivatives.

Preferably, the 3' OH group of the 3' nucleotide is esterified, preferably by a diester. The 3' OH group of the 3' nucleotide is esterified by the OH-group of any one of the following molecules including a 3' Spacer 18, 3' Spacer 9, 3' C3-Spacer, 3' C6-Spacer, 3' abasic residues (d spacer, r spacer), 3' C6-amino-linker, a 3' C12-amino-linker, and any functional analog thereof.

In some embodiments, the above mentioned blocking moieties may be introduced in that an oligonucleotide is ligated to the single-stranded cDNA, preferably by using a T4 RNA ligase, whereby said oligonucleotide contains any of the above mentioned blocking moieties at its 3' terminus, preferably 3' terminal 3' OH group, which block ligation.

After the optional end-repair step and the generation of the second strand, a so-called A-addition step may be carried out, which generates a terminal adenine as a docking site for sequencing adapters that may have an overhang formed by thymidine nucleotides, i.e. a T-overhang.

In some embodiments, the docking of the end-repaired RNA to the sequencing adaptors may be achieved by blunt end cloning, whereby both the RNA and the adapter molecules have blunt ends. Preferably, the sequencing adapters are covalently coupled to a surface.

The A-overhang is added to the 3'-terminus of the PCR product, which may be end-repaired, e.g. by Klenow Fragment exo-, the large fragment of the DNA polymerase I having 5'→3' polymerase activity, but lacking both 3'→5' exonuclease activity and 5'→3' exonuclease activity. The A-addition step by using the Klenow Fragment exo- is preferably carried out at 37° C. for about 30 minutes. Inactivation of the enzyme is carried out at 75° C. for about 10 minutes.

Alternatively, the A-addition step can also be facilitated with enzymes having terminal nucleotide transferase activity, such as the Taq polymerase.

Following the optional A-addition step, the sequencing adapters can be ligated to the DNA by a ligase, such as the T4 DNA Ligase, T3 DNA ligase, or T7 DNA ligase, preferably T4 DNA ligase. Blunt-end ligation may be carried out with T4 DNA ligase or T3 DNA ligase, preferably T4 DNA ligase. The ligation is only effective on those strands, which do not comprise a 5' terminal random oligonucleotide comprising a blocking moiety as a constituent of the first strand (cDNA) sequence. Hence, only the second or the first strand may be attached to an adapter by TA-ligation at its 5'- and 3' termini, depending on whether the single-stranded cDNA generation with the reverse transcriptase or the generation of the second DNA strand is carried out in the presence of oligonucleotides comprising a blocking moiety. In some embodiments, where both the 5'- and 3' termini of the first DNA strand are coupled to a ligation inhibiting moiety (blocking moiety), the adapters may only attach to the second DNA strand.

Preferably, the adapters, which attach to the first or the second DNA strand at its 3' and 5' termini, are not the same.

In preferred embodiments, the ligation to sequencing adapters is carried out by applying the GeneRead Library Prep Kit (QIAGEN) according to the manufacturer's instructions. The ligated products are preferably purified with the GeneRead Size Selection Kit (QIAGEN) and PCR amplified for 10 or more cycles by using the GeneRead Library Amplification Kit (QIAGEN).

In some embodiments, the above methods further comprise a purification step for the purification of the RT reaction. Preferably, said purification reaction is carried out with a QIAquick Nucleotide Removal Kit (QIAGEN). Said methods may further comprise a PCR purification step, which is used after the generation of the second DNA strand and the optional end-repair reactions. Said methods may comprise a further purification step, which is applied after the adapter-ligation step and before conducting the sequencing and sequence analysis. Preferably, the GeneRead size Selection kit is selected for such a purification step.

In some embodiments, the sequencing may be carried out by applying paired-end sequencing. Such sequencing enables sequence analysis, which is initiated from both dsDNA ends. In preferred embodiments, the adapter-ligated strands generated from fragments may be applied to a solid surface, such as on the Illumina® (Solexa) sequencer, more preferably the MiSeq sequencer. Each of the two adapter sequences is complementary to the respective surface-bound amplification primer on the flow cells.

Kits

Another aspect of the invention refers to kits, wherein such kits comprise (i) oligonucleotide primers comprising a moiety covalently coupled to the 5' terminal nucleotide, which blocks the ligation of the DNA to sequencing adapters;
(ii) unmodified primer oligonucleotides;
(iii) a reverse transcriptase; and
(iv) optionally a DNA polymerase.

In some embodiments the kits further include a buffer, which allows for effective reverse transcription activity of the reverse transcriptase. Such a buffer has a pH ranging from 7.5-9.0, preferably, 8.0-8.5, more preferably of about 8.3. Suitable buffers include Tris-HCl (about 50 mM at 25° C.). 40-75 mM KCl, 3-10 mM $MgCl_2$, more preferably 7 mM $MgCl_2$, and about 1-10 mM DTT.

In some embodiments, the kits referred herein further comprise:

(v) a polynucleotide kinase and an enzyme with polymerase and exonuclease activities;

(vi) optionally a deoxynucleotidyl transferase enzyme;

(vii) two adapters, which optionally comprise a terminal thymine, for ligation to the end-repaired DNA strands, each of which is complementary to a surface-bound amplification primer, respectively; and (viii) a ligase.

In some embodiments, the oligonucleotide primers, which are covalently coupled to a moiety, which blocks ligation or unmodified oligonucleotide primers, are random oligonucleotide primers.

In some embodiments of the above kits, the reverse transcriptase is selected from any one of a retroviral reverse transcriptase, retrotransposon reverse transcriptase, hepatitis B reverse transcriptase, cauliflower mosaic virus reverse transcriptase, murine leukemia virus reverse transcriptase, avian myeoloblastosis virus (AMV), bacterial reverse transcriptase, Tth DNA polymerase, or Taq DNA polymerase.

In some embodiments, the DNA polymerase is a DNA Polymerase I, the polynucleotide kinase is a T4 Polynucleotide Kinase, the enzyme with polymerase and exonuclease activities is a T4 DNA Polymerase and the deoxynucleotidyl transferase enzyme is Klenow fragment exo-.

In some embodiments, suitable buffer conditions in the kit for the simultaneous generation of the second strand and end-repairing comprise or consist of 10-30 mM Tris-HCl, 8-15 mM $(NH_4)_2SO_4$, 2-10 mM $MgCl_2$, 01-0.2 β-NAD, each at pH 7.4 at 25° C. Preferably, the buffer conditions comprise or consist of about 20 mM Tris-HCl, about 12 mM $(NH_4)_2SO_4$, about 5 mM $MgCl_2$, about 0.16 β-NAD, each at about pH 7.0-7.6, preferably 7.4 at 25° C.

In some embodiments, the kit may further include a buffer for effective enzymatic activity of the ligase, whereby such a buffer comprises or consists of about 50 mM Tris-HCl, about 10 mM $MgCl_2$, about 1 mM ATP, and about 10 mM DTT, each at about pH 7.5 at 25° C.

In preferred embodiments of the above kits, the oligonucleotides are covalently coupled to a blocking moiety in a way as to block a ligation reaction at the 5' terminal nucleotide, more specifically, at the 5' phosphate of the 5' terminal nucleotide. More preferably, the ligation is blocked to adapters for subsequent sequencing.

More specifically, these oligonucleotides covalently coupled to a blocking moiety do not possess a free 5' phosphate group at their 5' end, the base of the 5' terminal oligonucleotide is not any one of thymine, adenine, cytosine, guanine and uracil; one or both 2' hydrogens of the deoxyribose of the 5' terminal nucleotide is/are replaced by another atom or a blocking moiety; and/or the oligonucleotide comprises a 5' terminal nucleotide having a pentose in a sterical conformation, which is other than that of ribose or deoxyribose in RNA or DNA. Preferably, such pentose molecules include but are not restricted to arabinose.

In some embodiments, the oligonucleotide primers comprising a covalently coupled moiety, which blocks ligation, comprise a 5' OH or a free 5' phosphate group at the 5' terminal nucleotide before being covalently coupled to a blocking moiety.

In some embodiments, the unmodified oligonucleotide primers are phosphorylated at their 5' termini and the oligonucleotide primers comprising a covalently coupled moiety, which blocks ligation, comprise a 5' OH or a free 5' phosphate group at the 5' terminal nucleotide, which is covalently coupled to a moiety.

In some embodiments of the above methods or kits, the 5' phosphate group of the deoxyribose of the 5' terminal nucleotide of the oligonucleotide primer comprising a covalently coupled moiety, which blocks ligation, is esterified, or the 5' OH group of the 5' terminal nucleotide of the oligonucleotide primer, which blocks ligation, is esterified or etherified.

In some embodiments of the above methods or kits, the 5' phosphate group of the oligonucleotide primer comprising a covalently coupled moiety, which blocks ligation, is esterified by an alkyl or aryl alcohol, or the 5' OH group of the oligonucleotide primer, which blocks ligation, is esterified by a monoalkyl phosphate, dialkyl phosphate, monoalkyl- or dialkyl phosphothionate, or by a boronic acid.

In some embodiments, the 5' phosphate group of the 5' nucleotide is esterified by a diester bond between the phosphate group of the pentose, preferably deoxyribose of the 5' terminal nucleotide of the oligonucleotide primer and a hydroxyl group of hydrocarbon comprising at least one OH group, preferably an aryl or alkyl alcohol, which comprises at least one OH group, more preferably a primary or secondary alkyl alcohol. In other embodiments, the OH group is an OH group of the 5'5' inverted nucleotide. The alkyl or aryl alcohol, preferably primary or secondary alkyl alcohol may further comprise at least one additional functional group. Preferably, such a functional group is selected from, but not restricted to a, mono- or polyether, mono- or polyester, carboxylate, primary amine or hydroxyl groups. The alkyl or aryl alcohol may comprise cyclic ethers, such as 2-methyl-tetrahydrofuran and its derivatives. In some embodiments, the monoalkyl or aryl alcohol, preferably primary or secondary alcohol, comprises a biotinyl group.

In some embodiments, the covalently coupled blocking moiety at the 5' OH group of the 5' nucleotide is selected from any of the following: 5'-spacers, such as 5' Spacer 18, 5' Spacer 9, 5' C3-Spacer, 5' C6-Spacer, 5' abasic residues (d spacer, r spacer), 5'-5' inverted nucleotides, and 5' linkers, such as DADE-linker, 5' C6-amino-linker, and 5' C12-amino-linker, and 5'-biotinylated C6, C12-amino-linker, and any functional analog thereof.

In some embodiments, an unmodified 5' terminal nucleotide is covalently coupled to any one of fludarabine, azathioprine, mercaptopurine, pentostatin, cladribine, floxuridine, gemcitabine, cytarabine, gemcitabine, capecitabine, and tegafur.

In some embodiments, the one or both 2' hydrogen(s) of the 5' nucleotide of the 5' terminus of an oligonucleotide is/are replaced by an atom or moiety selected from, but not restricted to a halogen atom, preferably, F, Cl, Br, or I, or a C1-C5 alkyl or C1-C5 alkoxy group, preferably C1-C3 alkyl or C1-C3 alkoxy group, which may or may not comprise one or more additional functional groups.

In some embodiments of the above kits, the 3' OH group of the pentose, preferably deoxyribose of the 3' terminal nucleotide of the generated first DNA strand may be covalently coupled to a moiety, which blocks ligation. Preferably, the 3' OH group of the 3' nucleotide is esterified, more preferably by a diester.

In some embodiments of the kits, the covalent coupling of a blocking moiety at the 3' OH group of the 3' terminus consists of a hydrocarbon phosphate, preferably an alkyl or aryl phosphate, more preferably monoalkyl phosphate or a dialkyl phosphate. In other embodiments, the covalent coupling of a blocking moiety consists of a hydrocarbon phosphothionate, preferably an aryl or alkyl phosphothionate, more preferably monoalkyl phosphothionate or a dialkyl phosphothionate. In yet other embodiments, the covalent coupling of a blocking moiety consists of a boronic acid. In yet other embodiments, the modification is an aryl or alkyl phosphoboronate, more preferably monoalkyl or dialkyl phosphoboronate.

The alkyl phosphate, alkyl phosphothionate, or boronic acid preferably comprises at least one additional functional group, which is selected from a mono- or poly-ether, mono- or polyester, carboxylate, primary amine or hydroxyl groups. The monoalkyl or dialkyl phosphate may also comprise cyclic ethers, such as 2-methyl-tetrahydrofuran and its derivatives. Preferably, the 3' OH group of the 3' nucleotide is esterified, preferably by a diester. The 3' OH group of the 3' nucleotide is esterified by the OH-group of any one of the following molecules including a 3' Spacer 18, 3' Spacer 9, 3' C3-Spacer, 3' C6-Spacer, 3' abasic residues (d spacer, r spacer), 3' C6-amino-linker, a 3' C12-amino-linker, and any functional analog thereof.

In some embodiments, the above mentioned blocking moieties may be introduced in that an oligonucleotide is ligated to the single-stranded cDNA, preferably by using a T4 RNA ligase, whereby said oligonucleotide contains any of the above mentioned blocking moieties at its 3' terminus, preferably 3' terminal 3' OH group, which block ligation.

In some embodiments of the above kits, the kits may further comprise a purification kit for the purification of the RT reaction setup. Preferably, said purification kit is QIAquick Nucleotide Removal Kit (QIAGEN). Said kits may further comprise a PCR purification kit, which is used after the generation of the second DNA strand and the end-repair reactions. Preferably, the purification is carried out by applying the MinElute PCR Purification Kit (QIAGEN). Said kits may comprise a further purification step, which is applied after the adapter-ligation step. Preferably, the GeneRead Size Selection kit is selected for such a purification step.

EXAMPLES

RNA from HeLa cells is extracted with RNeasy kit (QIAGEN) and the PolyA+ mRNA is enriched with the GeneRead Pure mRNA Kit (QIAGEN). 86 ng of PolyA+ mRNA is then used in each RNA-Seq Library Prep reaction following the below protocol:

32 μl of mRNA (total amount: 86 ng) was mixed with 8 μl qScript Flex Reaction Mix (5×) (Quanta Biosciences), 2 μl random 8mer oligos (200 μM, IDT). The random oligos are either native oligos ('Control'), or oligos with a C3 spacer on the 5' ('Mod', /5SpC3/NNN NNN NN, IDT)), which will block the ligation of the resulting cDNA to sequencing adapter.

The mRNA/random oligo mix is heated at 94° C. for 15 minutes to fragment the RNA to an average size of about 100-200 bp. After the heat-mediated fragmentation, the mix is cooled down on ice.

Subsequently, reverse transcription (RT) components are added: 2 μl of RNAse Inhibitor (4 U/μl, QIAGEN), 2 μl of dNTPs (10 mM each, QIAGEN), 4 μl of DTT (0.1 M), and 2 μl of qScript Reverse Transcriptase (Quanta BioSciences). The following temperature profile is used for the RT reaction: 25° C. for 10 minutes, 42° C. for 50 minutes, and 70° C. for 15 minutes to inactivate the enzyme.

Once the RT reaction is complete, the first strand cDNA synthesis reaction is purified with QIAquick Nucleotide Removal Kit (QIAGEN) before the cDNA is subjected to second strand synthesis, which contains purified first strand cDNA (in 40 μl eluate), 8 μl 10× NEB Second Strand Synthesis Reaction Buffer (New England Biolabs), 10 μl *E. coli* DNA ligase (10 U/μl, New England Biolabs), 4.8 μl DNA Polymerase 1 (5 U/μl, New England Biolabs), 4 μl RNase H (5 U/μl, New England Biolabs), 4 μl T4 Polynucleotide Kinase (10 U/μl, New England Biolabs), T4 DNA Polymerase (3 U/μl, New England Biolabs) and 5.2 μl of RNase-free water (QIAGEN) to make up the total reaction volume of 80 μl.

T4 Polynucleotide Kinase and T4 DNA Polymerase are added to facilitate the end-repair of the double-stranded cDNA and make them directly ready for ligation to sequencing adapters. The second-strand cDNA synthesis reaction is performed at 25° C. for 30 minutes and then heat-inactivated for 10 minutes at 70° C.

The reaction mix is purified with MinElute PCR Purification Kit (QIAGEN) and eluted in 25 μl water. 3 μl of Klenow (exo-) and 3 μl of 10× A-addition buffer (both from GeneRead Library Prep Kit, QIAGEN) are added to the 25 μl elute and the A-addition reaction is performed at 37° C. for 30 minutes and inactivated at 75° C. for 10 minutes.

The adapter ligation reaction is then conducted with GeneRead Library Adapters for Illumina Sequencers (QIAGEN), the ligation buffer and ligase from the GeneRead Library Prep kit (QIAGEN) according to the manufacturer's instructions. The workflow for the above-referenced process is displayed in FIG. 1.

The ligated sequencing library is purified with GeneRead Size Selection kit (QIAGEN) and PCR-amplified for 10 cycles (GeneRead Library Amplification kit, QIAGEN).

Both libraries are then sequenced on miSeq instrument with the MiSeq Reagent Kit V2 (300 nt) by applying paired-end sequencing. Sequencing data are analyzed with the CLC Genomics Workbench (QIAGEN).

Figure 2:
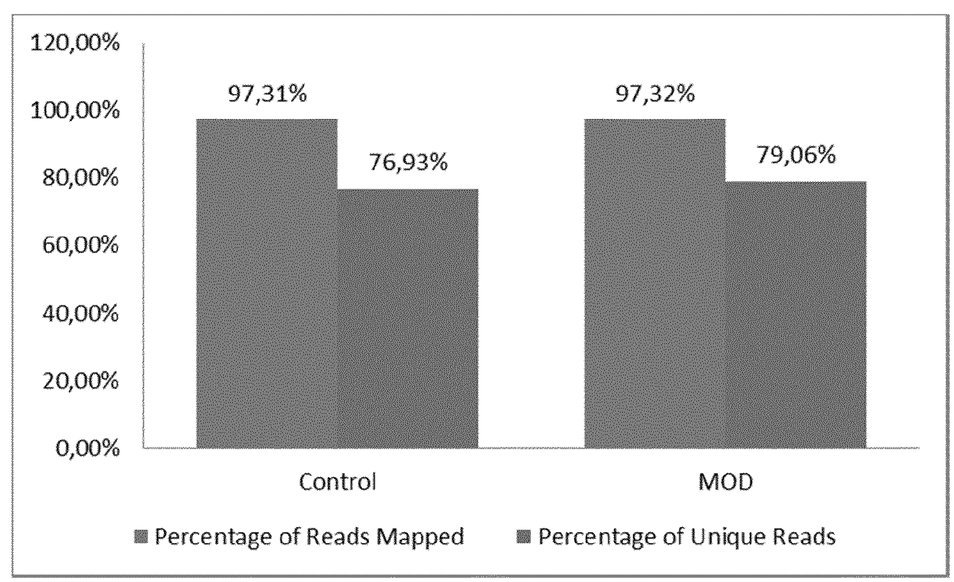
FIG. 2: High percentage of mapped reads and unique reads is shown for both control ('Control') libraries and ('MOD') RNA-Seq libraries, which were generated by using oligonucleotides, which are covalently coupled to a blocking moiety.

As shown in FIG. 2, both libraries have high percentage of reads that were mapped to human genome reference hg19 (97.31% and 97.32%), as well as unique reads (76.93% and 79.06%), demonstrating good library quality.

Figure 3:
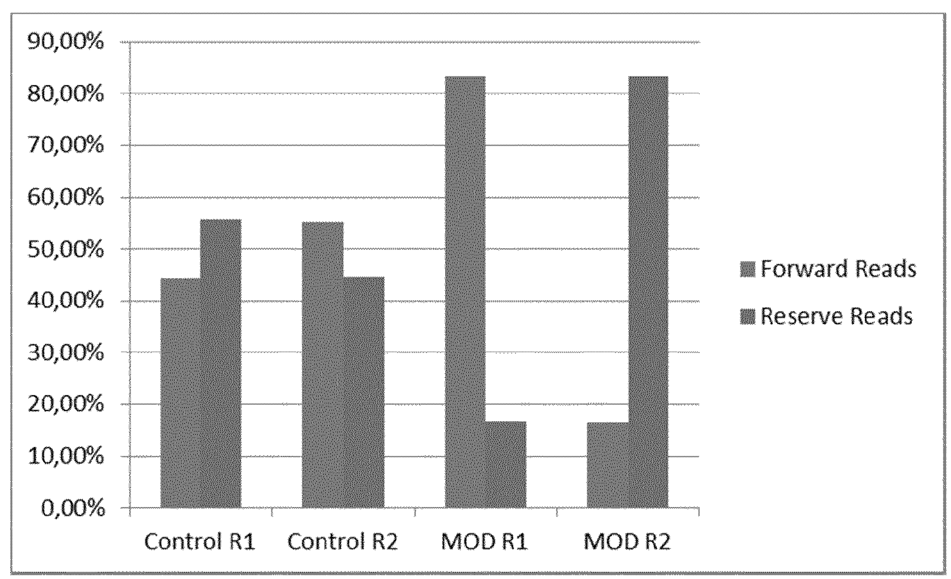
FIG. 3: The strand-specificity of the RNA-Seq libraries.

Strand specificity of both libraries is examined. As shown in FIG. 3, the first reads of the library generated with random oligos covalently coupled to a blocking moiety (MOD, R1) are predominantly mapped to the forward strand of the reference, while the second reads (MOD, R2) are predominantly mapped to the reverse strand. In contrast, the mapping of either R1 or R2 of the control library is relatively balanced for forward vs reverse strand.

Figure 4:
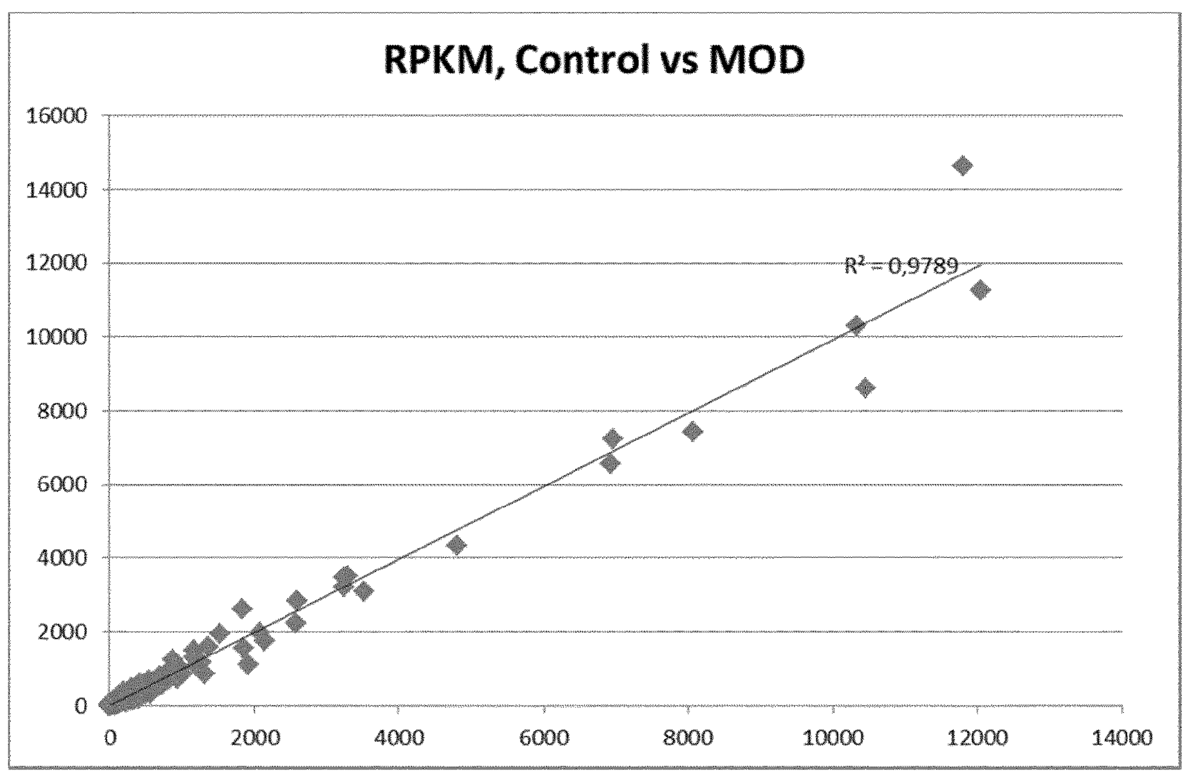
FIG. 4: RPKM (Reads Per Kilobase of transcript per Million reads mapped). Control Library is plotted on the X-axis versus the corresponding RPKM from RNA-Seq Library, which is generated with random oligonucleotides, which are covalently coupled to a blocking moiety, in a RT reaction on the Y-axis. The R^2 of 97.89% indicates a high correlation in transcript quantification of both RNA-seq library prep methods.

A comparison of the RPKM (R̈eads P̈er K̈ilobase of transcript per M̈illion reads mapped) demonstrates high degree of agreement between the two libraries (R^2 of 97.89%, FIG. 4, RPKM from Control Library: X-axis; RPKM from stranded RNA-Seq Library: MOD), suggesting that the stranded RNA-Seq library does not alter gene expression profiling results compared to the control, standard RNA-seq library.

Taken together, a novel method is shown that has minimal deviation from the standard RNA-Seq library prep protocol in procedure, but is able to generate strand-specific RNA-Seq libraries without introducing additional enzymatic reaction steps in the workflow.

The invention claimed is:

1. A method of RNA sequencing comprising:

(i) providing RNA;

(ii) generating a single-stranded DNA comprising a first DNA strand, which is complementary to the RNA of (i), by subjecting the RNA of (i) to reverse transcription using a reverse transcriptase and a first set of random oligonucleotide primers;

(iii) generating a double-stranded DNA comprising the first DNA strand and a second DNA strand using a DNA polymerase, a second set of random oligonucleotide primers, and the single-stranded DNA generated in (ii);

(iv) ligating adapters to the double-stranded DNA of (iii) to obtain a generated DNA; and (v) sequencing the generated DNA;

wherein either:

a) the first set of random oligonucleotide primers comprises a covalently coupled moiety at its/their 5' terminal nucleotide, which blocks ligation at a 5' terminus of the first DNA strand of the single-stranded DNA generated in (ii); or b) the second set of random oligonucleotide primers comprises a covalently coupled moiety at its/their 5' terminal nucleotide, which blocks ligation at a 5' terminus of the second DNA strand of the double-stranded DNA generated in (iii);

wherein a) and b) are mutually exclusive; and wherein the reverse transcriptase is selected from a group consisting of retroviral reverse transcriptase, retrotransposon reverse transcriptase, hepatitis B reverse transcriptase, cauliflower mosaic virus reverse transcriptase, murine leukemia virus reverse transcriptase, avian myeoloblastosis virus (AMV), bacterial reverse transcriptase, Tth DNA polymerase and a Taq DNA polymerase.

2. The method of claim 1, further comprising, prior to step (iv):

(iii)(a) end-repairing the double-stranded DNA using a polynucleotide kinase and an enzyme with polymerase and exonuclease activities to obtain end-repaired DNA strands.

3. The method of claim 2, further comprising, after (iii)(a):

(iii)(b) adding a terminal adenine to 3' termini of the double-stranded DNA using a deoxynucleotidyl transferase enzyme, wherein the adapters comprise 3' terminal thymines, which in (iv) ligate to double-stranded DNA comprising 3' terminal adenines.

4. The method according to claim 1, wherein the covalently coupled moiety at the 5' terminal nucleotide of the second set of random oligonucleotide primers, which blocks ligation, is selected from a group consisting of 5' Spacer 18, 5' Spacer 9, 5' C3-Spacer, 5' C6-Spacer, 5' abasic residues, 5'-5' inverted nucleotides, DADE-linker, 5' C6-amino-linker, 5' C12-amino-linker, 5'-biotinylated 5' C6 and 5' C12-amino-linker.

5. The method according to claim 1, wherein the generated first DNA strand of the single-stranded DNA, which comprises the covalently coupled moiety, which blocks ligation at the 5' terminus, further comprises a modification at its 3' terminus, which blocks ligation at said 3' terminus and which is introduced after the generation of the first DNA strand of the single-stranded DNA.

* * * * *